(12) United States Patent
Castro

(10) Patent No.: US 6,743,578 B1
(45) Date of Patent: Jun. 1, 2004

(54) METHOD FOR THE DETECTION OF SPECIFIC NUCLEIC ACID SEQUENCES BY POLYMERASE NUCLEOTIDE INCORPORATION

(75) Inventor: Alonso Castro, Santa Fe, NM (US)

(73) Assignee: The Regents of the University of California, Los Alamos, NM (US)

( * ) Notice: Subject to any disclaimer, the term of this patent is extended or adjusted under 35 U.S.C. 154(b) by 361 days.

(21) Appl. No.: 09/454,385

(22) Filed: Dec. 3, 1999

Related U.S. Application Data

(60) Provisional application No. 60/113,139, filed on Dec. 18, 1998.

(51) Int. Cl.$^7$ .............. C12Q 1/68; C12P 19/34; C07H 21/02
(52) U.S. Cl. ............... 435/6; 435/91.1; 435/91.2; 536/23.1; 536/24.33
(58) Field of Search .............. 435/6, 91.1, 91.2; 536/23.1, 24.33; 935/77

(56) References Cited

U.S. PATENT DOCUMENTS

| | | | |
|---|---|---|---|
| 4,683,195 A | | 7/1987 | Mullis et al. ............ 435/6 |
| 5,209,834 A | | 5/1993 | Shera |
| 5,518,900 A | | 5/1996 | Nikiforov et al. ......... 435/91.1 |
| 5,558,998 A | * | 9/1996 | Hammond et al. ......... 435/6 |
| 5,652,099 A | * | 7/1997 | Conrad ................. 435/6 |
| 5,736,332 A | * | 4/1998 | Mandecki ............... 435/6 |
| 5,888,819 A | * | 3/1999 | Goelet et al. ............ 435/5 |
| 6,004,744 A | | 12/1999 | Goelet et al. ............ 435/5 |
| 6,265,163 B1 | * | 7/2001 | Albrecht et al. ........... 435/6 |

OTHER PUBLICATIONS

Chang H. In situ transcription with Tth DNA polymerase and fluorescent nucleotides Journal of Immunological Methds vol. 176, pp. 235–243, Aug. 1994.*
Castro A. single–Molecule electrophoresis. Anal. Chemistry. vol. 67, pp. 3181–3186, Aug, 1994.*
Chang, "In Situ Transcription with Tth DNA Polymerase and Fluorescent Nucleotides," Journal of Immunological Methods, 176 pp. 235–243, 1994.
Peter M. Goodwin et al., "Single Molecule Identification Using Selected Fluorescence Characteristics," U.S. patent application S.N. 09/169,025, filed Oct. 9, 1998.
Alonso Castro et al., "Single–Molecule Detection of Specific Nucleic Acid Sequences in Unamplified Genomic DNA," Analytical Chemistry 69, 3915 (1997).
Alonso Castro et al., "Single–Molecule Electrophoresis," Analytical Chemistry 67, 3181 (1995).

* cited by examiner

Primary Examiner—Jeffrey Fredman
(74) Attorney, Agent, or Firm—Ray G. Wilson

(57) ABSTRACT

A method for rapid and efficient detection of a target DNA or RNA sequence is provided. A primer having a 3'-hydroxyl group at one end and having a sequence of nucleotides sufficiently homologous with an identifying sequence of nucleotides in the target DNA is selected. The primer is hybridized to the identifying sequence of nucleotides on the DNA or RNA sequence and a reporter molecule is synthesized on the target sequence by progressively binding complementary nucleotides to the primer, where the complementary nucleotides include nucleotides labeled with a fluorophore. Fluorescence emitted by fluorophores on single reporter molecules is detected to identify the target DNA or RNA sequence.

12 Claims, 3 Drawing Sheets

DNA target

↓ Denature

↓ Hybridize to primer

Primer

↓ Extend using polymerase

Labeled nucleotides    Polymerase

Free nucleotides

↓ Final product

Fluorescent reporter

SEQUENCE LISTING

<160> NUMBER OF SEQ ID NOS: 1

<210> SEQ ID NO 1
<211> LENGTH: 24
<212> TYPE: DNA
<213> ORGANISM: pUC19

<400> SEQUENCE: 1
cgccagggtt ttcccagtca cgac                                          24

METHOD FOR THE DETECTION OF SPECIFIC NUCLEIC ACID SEQUENCES BY POLYMERASE NUCLEOTIDE INCORPORATION

RELATED APPLICATION

This application claims the benefit of U.S. Provisional Application Ser. No. 60/113,139, filed Dec. 18, 1998.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to detection of nucleic acid sequences, and, more particularly, to the selective incorporation of fluorescent markers to detect nucleic acid sequences.

BACKGROUND OF THE INVENTION

The rapid and efficient detection of specific nucleic acid sequences in biological samples plays a central role in a variety of fields, including molecular biology, biotechnology, immunology, medical diagnosis, forensic analysis, and quality control of food products. One of the most commonly used techniques for the detection of specific nucleic acid sequences is the Southern blot. This is a hybridization technique in which the fragments to be interrogated have been size-separated by gel electrophoresis and transferred from the gel to a nylon nitrocellulose filter. A radioactive probe is then added to the filter so that hybridization takes place. After washing away the excess probe, the band containing the target nucleic acid is detected by exposing an x-ray film to the filter.

Despite its popularity, Southern blotting suffers from some limitations: it involves a series of manually intensive procedures that cannot be run unattended and cannot be readily automated. The process for separating the fragments by gel electrophoresis and subsequently detecting the bands by autoradiography are time-consuming tasks that are susceptible to poor quantitative accuracy and poor reproducibility.

The use of radioactive probes brings up a set of safety and environmental concerns. The lack of adequate sensitivity is another limitation, which has been partially addressed by the development of the polymerase chain reaction (PCR) and related target amplification methods. The PCR consists of selectively amplifying a target DNA sequence in a sample. Amplification products are usually detected by dyes that stain nucleic acids or by hybridization with sequence-specific probes. Amplification methods, however, may introduce ambiguities resulting from contamination or from variability in amplification efficiency. Therefore, there is a need for robust analytical methods that provide accurate quantitation and molecular weight estimates for target DNA or RNA segments.

Various objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the present invention includes a method for identifying a target DNA or RNA sequence. A primer having a 3'-hydroxyl group at one end and having a sequence of nucleotides sufficiently homologous to hybridize with an identifying sequence of nucleotides in the target DNA or RNA is selected. The primer is hybridized to the identifying sequence of nucleotides and a reporter molecule is synthesized on the target sequence by extending the primer by progressively binding nucleotides to the primer that are complementary to the corresponding nucleotides of the DNA or RNA sequence, where the complementary nucleotides include nucleotides labeled with a fluorophore. Fluorescence emitted by fluorophores on individual reporter molecules is detected to identify the target DNA or RNA sequence.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION

In accordance with the present invention, a new method enables the direct detection of specific nucleic acid sequences in biological samples. The basis of the approach is to monitor for the presence of a specific nucleic acid sequence of bacterial, human, plant or other origin. The nucleic acid sequence may be a DNA or RNA sequence, and may be characteristic of a specific taxonomic group, a specific physiological function, or a specific genetic trait.

Figure 1A:
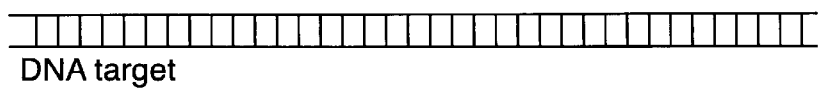
FIGS. 1A–1E schematically depict the process of the present invention.
Figure 1B:
Figure 1C:
Figure 1D:
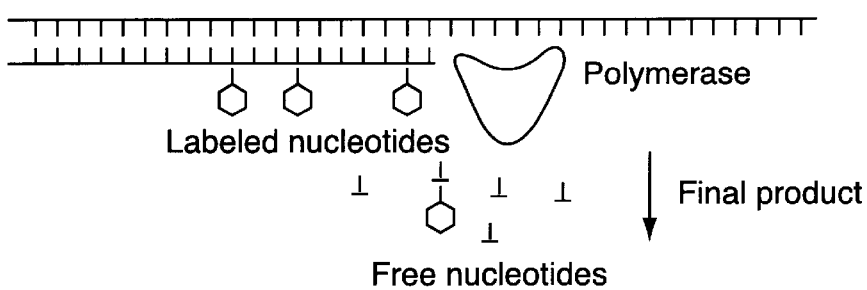
Figure 1E:
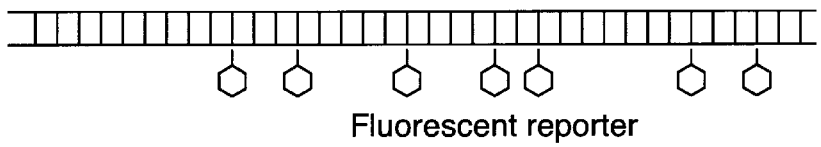

The method consists of synthesizing in vitro a fluorescent nucleic acid reporter molecule using a relatively short sequence of the target as a template as shown in FIGS. 1A–1E. A DNA target (FIG. 1A) is denatured according to well known processes to form a single stranded DNA target (FIG. 1B). A short oligonucleotide primer that is specific and complementary to the target is then hybridized to the single stranded DNA target. A suitable polymerase and free nucleotides are added to the sample. One of these oligonucleotides is at least partially labeled with a fluorophore. If the target is present in the sample, the primer binds to an identifying sequence of the target, (FIG. 1C) and the polymerase will incorporate the labeled and unlabeled nucleotides (FIG. 1D) to reconstruct the target's complementary sequence as shown in FIG. 1E. If the labeled nucleotide concentration is kept below that of the unlabeled nucleotides, most of the labeled nucleotides will be incorporated into the reporter DNA molecule. Nonetheless, some free (i.e., unbound) labeled nucleotides will remain in the reaction mixture, but fluorescence from each synthesized reporter molecule will be much stronger than that of the free nucleotide background over the single-molecule detection time.

The sample is analyzed in a single molecule detection apparatus, as are well known and described in the art. Detection of the synthesized reporter molecule signifies the presence of the target being sought. The fluorescent signal from the reporter molecule is much larger than that of the background fluorescence originating from free labeled nucleotides, since the reaction is allowed to proceed until the reporter molecule is hundreds or thousands of bases long. The new method described here combines the advantages of flow-based analytical systems (system automation, speed, reproducibility) with the unsurpassed sensitivity of single-molecule detection. The sensitivity of this method allows for the direct detection of specific genes without the need for using amplification methods such as PCR and exhibits advantages over current methodologies in terms of sensitivity, speed and per-assay-cost. The non-radioactive approach for the ultrasensitive detection of specific sequences described here has applications in a wide variety of fields, such as gene identification, gene mapping, medical diagnostics, and biotechnology.

Exemplary Process

As an example, experiments were performed for the detection of pUC19 DNA, (a 2686 base-pair plasmid). Prior to all experiments, pUC19 DNA was digested with the restriction endonuclease Bgl I, which yields two fragments, 1568 bp and 1118 bp in length. As a control, identical experiments were run except that pUC19 DNA was substituted with lambda DNA. A specific sequence of the 1568-bp pUC19 fragment was detected at the single-molecule level of sensitivity. The lambda DNA control yielded negative results.

a. Primer design.

Primer sequences should be specific to the target being sought. Primers are typically 15–30 nucleotides long. Primer lengths greater than 15 nucleotides ensure that they will not anneal specifically to non-target nucleic acid. Generally, primer sequences have the following characteristics:

1. No internal secondary structures that impede hybridization and extension.
2. Balanced distribution of G/C and A/T rich domains (45–55%).
3. For the example experiment, we used the following 24-mer primer, which anneals to nucleotides 352–375 of pUC19:

5'-d(CGC-CAG-GGT-TTT-CCC-AGT-CAC-GAC)-3' (SEQ ID 1)

b. Nucleic acid extraction and isolation.

Common extraction methods, such as phenol extraction, can be used to isolate the DNA from the sample under investigation. See, for example, Reference 1 for nucleic acid extraction protocols.

c. Reporter synthesis.

i. Reagents:

| Name | Initial Conc. | Volume | Final Concentration | Source |
|---|---|---|---|---|
| Buffer | 10X | 5 uL | 1.0X | Promega Core System II cat. # M7665 |
| pUC19 DNA (2686 bp) digestion product (diluted 1:25) | 40 ng/uL | 4 uL | 3.2 ng/uL (160 ng/50 uL) 1.83 E-9 M | N.E. Biolabs cat. # 304-1S |
| Primer | 10 ng/uL 1.26 pmol/uL | 4 uL | 0.1 uM (5 pmol) | Promega cat. # Q5601 |
| Nucleotide mixture | | 1 uL | 20 uM each | |
| DATP | 1 mM | | | Promega cat # U1330 |
| DCTP | 1 mM | | | Promega cat # U1330 |
| DGTP | 1 mM | | | Promega cat # U1330 |
| DTTP | 0.8 mM | | | Promega cat # U1330 |
| Bodipy-TMR-14-dUTP | 0.2 mM | | | Molecular Probes cat. # C-7616 |
| Taq polymerase | 5 u/uL | 0.25 uL | 1.25 u/50 ul | Promega Core System II |
| MgCl2 | 25 mM | 3 uL | 1.5 mM | Promega Core System II |
| Distilled Water | | Complete to 50 uL | | | ii. Denature target DNA at 95° C. for 5 minutes.

iii. Mix all reagents gently and thoroughly. Add enzyme last. Centrifuge briefly to collect sample at bottom of tube.

iv. Extension: Incubate at 72° C. for 3 hours.

A proper temperature is selected for the hybridization of dNTP to extend the primer along the target; DNA molecule. If the temperature is too low, non-specific annealing will increase. An optimal hybridization temperature may be predicted for a given primer/target pair with available software routines, e.g., PRIMER, developed by The Whitehead Institute for Biomedical Research. For this example, the optimal temperature for Taq DNA polymerase activity is 72° C.

v. Optional: Add "STOP" solution to terminate enzymatic activity. If the reaction is not stopped, and the target is of suitable size, the amount of incorporated dye and, therefore, the reporter fluorescence intensity, will be proportional to the size of the fragment.

vi. Optional: remove free, unincorporated labeled nucleotides by physical means (e.g., precipitation, filtration, chromatography). In the exemplary results reported herein, a large fraction of the unincorporated labeled nucleotides were removed using a QIAquick Nucleotide Removal Kit (Quagen, Valencia, Calif.) following the manufacturer's protocols. Conversely, the primer can be labeled with a suitable immobilization group (e.g., biotin), which allows isolation of the reporter by physical means (e.g., solid support, magnetic beads).

d. Analysis by single-molecule detection.

Figure 2:
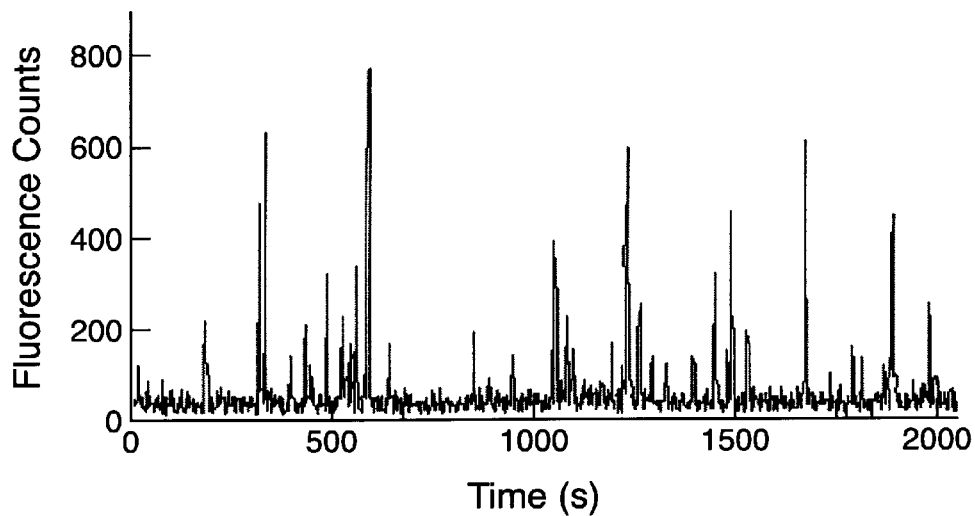
FIG. 2 graphically depicts the experimental results for the detection of a specific sequence of pUC19 DNA at the single-molecule level of sensitivity according to one embodiment of the present invention.
Figure 3:
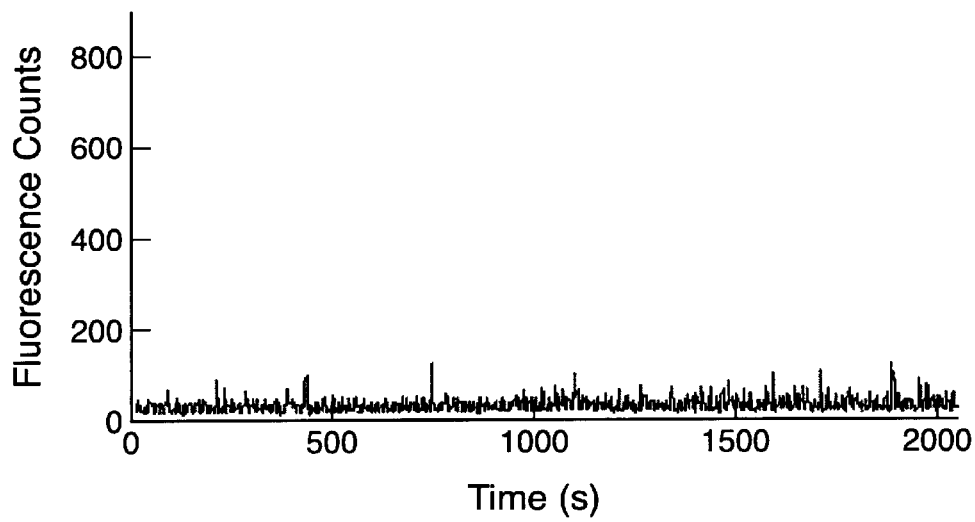
FIG. 3 graphically depicts results for a control experiment run under identical conditions as those corresponding to the experimental results shown in FIG. 2, except that the target was replaced by lambda DNA.

A single-molecule detection apparatus such as a variation of that described in References 2 and 3 or U.S. Pat. No. 5,209,834, issued May 11, 1993, is used to detect fluorescence from the reporter molecule. Suitable flow cytoometer apparatus and methods for single molecule detection are found in U.S. Pat. No. 5,558,998, issued Sep. 24, 1996, and U.S. patent application Ser. No. 09/169,025, filed Oct. 9, 1998, both incorporated by reference. Depending on reaction conditions, such as initial nucleotide concentration and temperature, it may or may not be necessary to remove unincorporated labeled nucleotide as explained in the Procedure section. In this example, the reaction mixture was diluted 1000-fold to 50 mL. This dilution yields a concentration of unincorporated nucleotide in the nanomolar range, and a concentration of reporter in the picomolar range. Therefore, when the sample is analyzed by single-molecule detection, the unincorporated nucleotide produces a constant background signal, and the reporter, which contains hundreds of labels, produces single fluorescence bursts with amplitudes well above that of the background. FIG. 2 shows the experimental results for the detection of pUC19 in this example. FIG. 3 shows the control experiments using lambda DNA as target.

Figure 4:
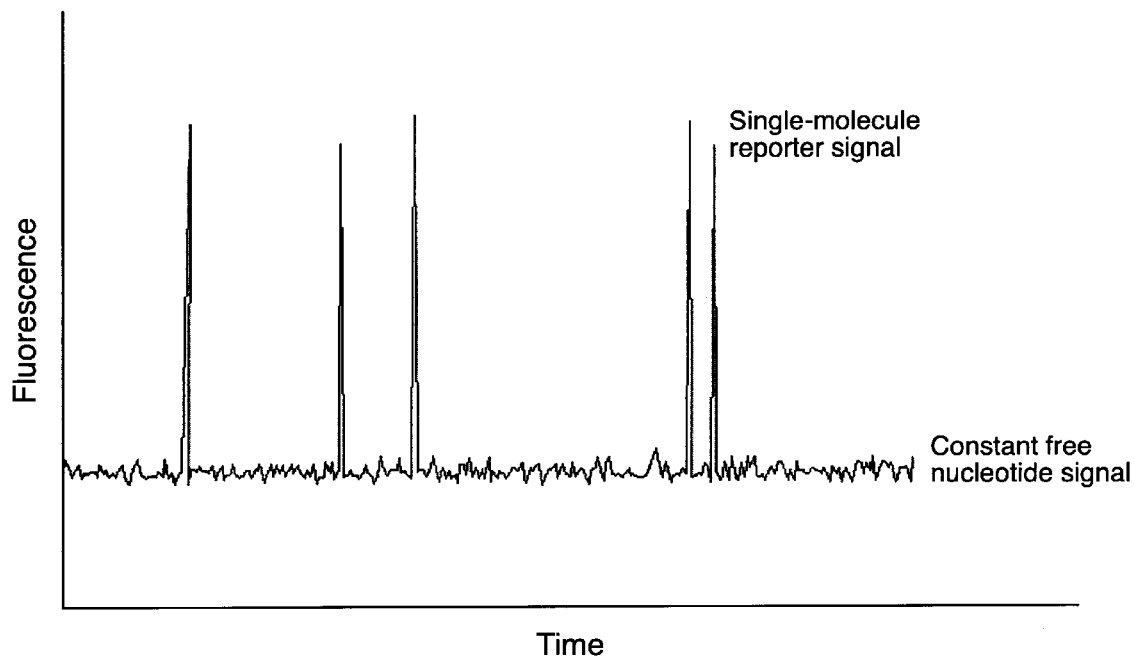
FIG. 4 graphically depicts a simulation of single molecule fluorescence signals from a reporter molecule according to a second embodiment of the present invention.

If the reporter synthesis reaction is allowed to proceed to completion, the amount of labeled nucleotide that is incorporated will be the same for identical targets. Therefore, each single-molecule burst will present the same amplitude, as shown in the simulation of FIG. 4, and a histogram of burst amplitudes will reveal the size of the target being sought.

e. Analysis by single-molecule electrophoresis.

Another way to avoid detecting interfering free nucleotides is to perform "single-molecule electrophoresis" (SME) as described in Reference 3 and in U.S. Pat. No. 5,209,834, incorporated by reference. In this method, the electrophoretic mobility of fluorescently labeled molecules (free labeled nucleotides and reporter molecules in this case) can be determined with single-molecule sensitivity. Since single nucleotides exhibit an elecrophoretic mobility vastly different to that of nucleic acid targets, interference from free nucleotides is eliminated. In addition, measuring the electrophoretic velocities of the targets present in the sample also permits the determination of their sizes, since their velocities are inversely proportional to the their length when electrophoresis is performed in an appropriate sieving medium.

REFERENCES

Incorporated Herein by Reference

1. "DNA Probes", G. Keller and M. Manak, Stockton Press, New York, 1993, section 2.
2. "Single-molecule detection of specific nucleic acid sequences in unamplified genomic DNA", A. Castro and J. G. K. Williams, Anal. Chem. 69, 3915–3920 (1997).
3. "Single-Molecule Electrophoresis". A. Castro and E. B. Shera, Anal. Chem. 67, 3181 (1995).

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for identifying single molecules having a target DNA or RNA sequence comprising the steps of:
    selecting a primer having a 3'-hydroxyl group at one end and having a sequence of nucleotides to specifically hybridize with an identifying sequence of nucleotides in the target DNA;
    hybridizing the primer to the identifying nucleotide sequences of the target DNA or RNA sequence;
    extending the primer along the target sequence by progressively binding a plurality of nucleotides to the primer that are complementary to the corresponding nucleotides on the target sequence to form a reporter molecule, where the complementary nucleotides include nucleotides labeled with a fluorophore; and
    detecting fluorescence emitted by fluorophores on individual reporter molecules by a process selected from the group consisting of flow cytometry and single molecule electrophoresis to identify the target DNA or RNA sequence.

2. A method according to claim 1, wherein the primer is at least about 15 nucleotides to specifically hybridize to the identifying sequence of nucleotides for the target DNA or RNA.

3. A method according to claim 1, including the steps of: forming a mixture of dATP, dGTP, dCTP, and dUTP nucleotides, where at least one of the nucleotide types is at least partially labeled with a fluorescent label;
    denaturing the target DNA or RNA;
    adding a polymerase that catalyzes the synthesis of the reporter molecule from the mixture of nucleotides; and
    incubating the mixture of nucleotides, target DNA or RNA, and polymerase for a time effective to extend the primer to a desired length.

4. A method according to claim 3, wherein the concentration of nucleotides in the mixture of nucleotides having a fluorescent label is less than the concentration of nucleotides without a fluorescent label.

5. A method according to claim 1, further including the step of removing free, unincorporated nucleotides after the binding reaction is completed.

6. A method according to claim 5, wherein the primer is at least about 15 nucleotides to specifically hybridize to the identifying sequence of nucleotides for the target DNA or RNA.

7. A method according to claim 5, including the steps of:
forming a mixture of dATP, dGTP, dCTP, and dUTP nucleotides, where at least one of the nucleotide types is at least partially labeled with a fluorescent label;
denaturing the target DNA or RNA;
adding a polymerase that catalyzes the synthesis of the reporter molecule from the mixture of nucleotides; and
incubating the mixture of nucleotides, target DNA or RNA, and polymerase for a time effective to extend the primer to a desired length.

8. A method according to claim 7, wherein the concentration of nucleotides in the mixture of nucleotides having a fluorescent label is less than the concentration of nucleotides without a fluorescent label.

9. A method according to claim 1, further including the step of measuring electrophoretic velocities of individual molecules present in the sample by single-molecule electrophoresis in order to separate the signals of free nucelotides from the reporter molecules.

10. A method according to claim 9, wherein the primer is at least about 15 nucleotides to specifically hybridize to the identifying sequence of nucleotides for the target DNA or RNA.

11. A method according to claim 9, including the steps of:
forming a mixture of dATP, dGTP, dCTP, and dUTP nucleotides, where at least one of the nucleotide types is at least partially labeled with a fluorescent label;
denaturing the target DNA or RNA;
adding a polymerase that catalyzes the synthesis of the reporter molecule from the mixture of nucleotides; and
incubating the mixture of nucleotides, target DNA or RNA, and polymerase for a time effective to extend the primer to a desired length.

12. A method according to claim 11, wherein the concentration of nucleotides in the mixture of nucleotides having a fluorescent label is less than the concentration of nucleotides without a fluorescent label.

* * * * *